(12) United States Patent
Jaeger (10) Patent No.: US 6,860,162 B1
(45) Date of Patent: Mar. 1, 2005

(54) LIQUID SAMPLER AND METHOD

(76) Inventor: Ben E. Jaeger, 50 Hunter La., Bristol, IL (US) 60512

( * ) Notice: Subject to any disclaimer, the term of this patent is extended or adjusted under 35 U.S.C. 154(b) by 0 days.

(21) Appl. No.: 10/773,379

(22) Filed: Feb. 6, 2004

(51) Int. Cl.$^7$ ................................................ G01N 1/00
(52) U.S. Cl. .................................. 73/863.85; 73/863.86
(58) Field of Search ........................ 73/863.85, 863.86, 73/863.81

(56) References Cited

U.S. PATENT DOCUMENTS

| | | | | |
|---|---|---|---|---|
| 309,232 A | * | 12/1884 | Lennon .................... | 73/863.85 |
| 2,351,764 A | * | 6/1944 | Jarrett ...................... | 73/863.21 |
| 3,229,711 A | * | 1/1966 | Leopold, Jr. et al. ........ | 137/318 |
| 3,374,678 A | * | 3/1968 | McGuckin ................ | 73/863.85 |
| 3,534,613 A | * | 10/1970 | Travor et al. ............. | 73/863.85 |
| 3,747,411 A | * | 7/1973 | McDermott et al. ...... | 73/863.54 |
| 4,218,918 A | * | 8/1980 | Ueno et al. ............... | 73/863.81 |
| 4,294,124 A | | 10/1981 | Kalwaitis | |
| 4,852,412 A | * | 8/1989 | Hill .......................... | 73/863.85 |
| 5,905,213 A | | 5/1999 | Jaeger | |
| 6,792,818 B2 | * | 9/2004 | Jaeger ...................... | 73/863.86 |
| 2002/0166392 A1 | * | 11/2002 | Handel ..................... | 73/863.83 |

FOREIGN PATENT DOCUMENTS

GB 2197469 A * 5/1988 ............ G01N/1/02

* cited by examiner

*Primary Examiner*—Hezron Williams
*Assistant Examiner*—John Fitzgerald
(74) *Attorney, Agent, or Firm*—Pyle & Piontek (57) ABSTRACT

A sampler for obtaining wine samples from a wine holding tank is characterized by a manually operable sampler and a connecting device for coupling the sampler to an opening to the tank. The connecting device has open and closed states and the sampler is coupled to the connecting device while it is closed, after which the connecting device is opened to establish a path between the sampler and tank opening. A probe of the sampler, having a forward sample receiving inlet that may be opened and closed, is then manually extended, while its inlet is closed, through the connecting device and tank opening into and through lees deposited as a sediment layer in the region of the tank opening, until the probe inlet is positioned beyond the sediment layer and in wine that is relatively free of sediment. The probe inlet is then opened for flow of a sample of wine from the tank into the inlet and through and out of the probe to a collection container. After collection of the wine sample, the probe inlet is closed and the probe is retracted from the tank and connecting device. The connecting device may then be closed to interrupt the path between the sampler and tank opening, at which point the sampler may be disconnected from the connecting device for use in obtaining additional wine samples by being attached to connecting devices associated with each of a series of additional wine holding tanks.

44 Claims, 4 Drawing Sheets

LIQUID SAMPLER AND METHOD

BACKGROUND OF THE INVENTION

The present invention relates to apparatus for and a method of extracting samples of liquid product from a vessel, and in particular to apparatus for and a method of extracting samples of wine from wine holding tanks.

Wine is produced by fermenting grape juice or grape must which contains not only the juice, but also the seeds and skins of the grapes. When the grape sugar is fully consumed, fermentation is complete and wine is produced. While the basic elements of wine production are relatively simple, the manipulation of grapes, juice, must and wine in manners to yield desired flavors and aromas is difficult. Wine makers try to produce specific desirable aromas and flavors in wine, while at the same time minimizing those that are undesirable. It is also necessary that the wine acids and alcohol be controlled, since if wine is too acidic it may taste sour, while if its ethanol level is too high it will have a strong taste of alcohol. An important factor that contributes to a wine's character is the type of grapes used, which influence a wine's flavor, alcohol content, acidity and color. Red and white wine production is generally the same, except that in making white wine the juice from white grapes is separated from the skins prior to fermentation, while in making red wine red grapes are used and fermentation takes place in the presence of the grape skins, so that red pigments and other compounds in the skins are extracted during fermentation to impart a red color to the wine as well as other features. Red grapes may be fermented without the skins, in which case the limited amount off pigment released when the grapes are crushed yields a blush or rose wine that is light in color.

In producing wine, grapes harvested from a vineyard are mechanically crushed to separate the stems from the grapes and to crack open the grapes to release the juice. To make white wine, the must yielded by the crushing process is pressed to separate the juice from the skins, with the amount of pressure applied influencing what flavor compounds are extracted from the skins. The white grape juice obtained by pressing is then introduced into a fermentation tank. In producing red, the must from the crusher, which includes both the juice and skins, is transferred to a fermentation tank. The fermentation tanks are usually made of stainless steel or wood, with the material used and the temperature of fermentation influencing the character of the wine. A number of the aroma components of wine are volatile and leave the wine by evaporation, and as evaporation occurs faster at higher temperatures, to retain aroma characters in the wine, the temperature of fermentation is controlled, usually by direct cooling of the fermentation tanks.

Fermentation may be allowed to proceed by relying only on the yeast naturally present on the grape skins and in the wine making equipment, or yeast may be added to the must in a process known as inoculation, with the particular species of yeast used resulting in the presence of particular positive and negative aroma characters in wine. Yeast under stress produces hydrogen sulfide, and to avoid this undesirable quality rotten egg smell, nutrients may be added to the fermentation tank. Also influencing wine character are the duration of fermentation and naturally occurring microorganisms that may grow in the must or juice and affect the flavors and aromas of the wine. For example, lactic acid bacteria consume acids and reduce the wine's acidity, and also produce other aromas including the buttery smells found in wine. Steps may therefore be taken to restrict the growth of lactic acid bacteria, especially if the wine is already low in acidity or if the buttery smell would dash with other aromas of the wine. Another type of bacteria, acetobacter, can spoil the wine by converting alcohol to vinegar.

Wine appears cloudy after fermentation is complete, and the yeast and other solids in the wine are therefore allowed to settle to the bottom of the tank, forming sediment called the lees. The dear wine resulting from settling is then racked or drawn off the lees and stored in a clean cask. In a process called fining, the wine may be further clarified by adding ingredients that attract unwanted particles such as proteins that cause cloudiness and which then settle to the bottom of the cask for collection and removal.

Following fermentation and clarification the wine is aged. The manner in which wine is aged affects the flavors and aromas present in the finished wine. For example, wine aged in oak barrels picks up flavor and aroma characters from the oak, a desirable quality in some wines. Wine may also be aged under conditions which encourage loss of some of the volatile fruity compounds, so that the wine is then richer in other characters. Exposure to air during aging causes phenolic wine compounds to combine with each other and produce tannins that over time become large and form reddishbrown sediment in the bottle, reducing wine bitterness and astringency. The time for which wine is aged before bottling determines the extent to which these reactions occur, and even after bottling the wine may continue to slowly age for many years.

Because of the many different variables involved in the production of wine and the large number of different qualities that may be imparted to wine, it is essential that the wine be sampled at various stages of its production process in order that the characteristics it is developing might be detected and timely controlled to yield wine having specifically desired qualities. Prior to commencement of fermentation, the top of the fermentation tank is open and samples of the must mixture are readily available. Once fermentation begins, the tank is closed to prevent contamination of its contents, for example by airborne bacteria and molds, and the art contemplates that further samples then be obtained by withdrawal through a hose connection made through a bung opening located near the bottom of the tank and controlled by an inline ball valve. A problem with this sampling technique is that as the must ferments to produce wine and when the wine is subsequently allowed to clarify and age the lees, consisting of dead yeast cells and other solids, forms as a several inch thick sediment layer on the bottom and lower side walls of the tank in the region of the bung opening. As a result, wine samples withdrawn from the tank through the bung opening are contaminated by sediment, which can also enter and dog the hose and ball valve.

OBJECTS OF THE INVENTION

A primary object of the present invention is to provide a sampler for obtaining samples of must and/or wine in succession from a series of large wine holding tanks, while preventing the lees from entering and blocking the sampler and eliminating or at least minimizing the presence of the lees in the samples.

SUMMARY OF THE INVENTION

In accordance with the present invention, a sampling apparatus for obtaining samples of liquid product from an interior of a vessel comprises a sampler including a body having a bore with a forward opening, an elongate probe in the bore and having a passage with a forward inlet to the passage, means for opening and closing the probe passage inlet, and means for reciprocating the probe in the bore to extend the probe out of and to retract the probe into the forward opening of the bore. Also included is a connecting device for coupling the sampler to the vessel, the sampler being attachable to and detachable from the connecting device and the connecting device being operable between open and closed states respectively placing the sampler into and out of communication with the vessel interior and product therein. The sampler may be detached from the connecting device, without escape of product from the vessel interior, when the connecting device is in the closed state.

When the connecting device is in the open state, the reciprocating means is operable to extend the probe out of the sampler body bore forward opening and through the connecting device into the vessel to a sampling position of the probe where the probe passage inlet is in liquid product in the vessel, and to then retract the probe from the vessel and through the connecting device and sampler body bore. While the reciprocating means extends the probe to the sampling position, the opening and closing means closes the probe inlet, following which the opening and closing means opens the probe inlet, while the probe is in the sampling position, for flow of a sample of liquid product from the vessel interior into the probe inlet and through the probe passage to a sample collection point. The opening and closing means then closes the probe inlet while the probe is being retracted from the vessel interior and through the connecting device and sampler body bore. Consequently, the only liquid product entering the probe inlet is that present in the area of the probe inlet when the probe is in its sampling position.

In an intended use, the sampling apparatus obtains a sample of wine from a wine holding tank. By virtue of the probe passage inlet being closed during extension and retraction of the probe into and from the tank interior, the lees that forms as a several inch thick sediment layer in the tank does not enter the inlet and contaminate the sample as the probe passes in both directions through the sediment layer incident to extension and retraction of the probe inlet into and from wine to be sampled inward from the sediment layer. In addition, because the connecting device is operable between open and closed states to place the sampler into and out of communication with the vessel interior, when the probe is retracted, the connecting device can be closed to allow the sampler to be detached from it without an outflow of wine from the tank, so that the same sampler can be moved from wine tank to wine tank and used to obtain wine samples in succession from a series of wine holding tanks.

The invention also contemplates a method of obtaining samples of liquid product from a vessel, and in the case where the liquid product is wine in a tank, the invention comprises the steps of mounting a connecting device to a wine tank at an opening to the tank; attaching a sampler to the connecting device; and establishing a path through the connecting device between the sampler and the tank opening. Also included are the steps of extending a probe of the sampler, having an inlet thereto, through the connecting device and tank opening into the tank-interior to position the probe inlet in wine in the tank, while maintaining the probe inlet closed; opening the probe inlet once the inlet is in the wine in the tank for flow of a sample of wine through the inlet into the probe; closing the inlet after obtaining the sample of wine; and then retracting the probe from the tank interior and through the tank opening and connecting device. Because the probe inlet is closed while the probe is extended into and retracted from the interior of the tank, as the probe passes through a sediment layer of the lees that normally accumulates in the lower end of the tank in the region of the tank opening, the lees does not enter the inlet and either block the probe or contaminate the wine sample.

The foregoing and other objects, advantages and features of the invention will become apparent upon a consideration of the following detailed description, when taken in conjunction with the accompanying drawings.

DETAILED DESCRIPTION

In general terms, the invention is a liquid product sampling apparatus comprising a tubular sampler body having a bore within which a tubular probe is reciprocated. The sampler body is adapted to be coupled by a connecting device to an opening to a vessel containing liquid product, and the probe is extended through the body bore, connecting device and vessel opening to a sampling position of the probe, where an inlet to the probe is within liquid product in the vessel interior. A plunger is in a passage through the probe and is reciprocated relative to the probe to open and close the probe inlet. The plunger has a forward tip that acts as a valve to close the probe inlet when the plunger is retracted. When the probe is in its sampling position, the plunger is moved forward to open the probe inlet for flow of a sample of liquid product from the vessel into the inlet and through the probe to a sample outlet opening from the probe. After the sample is obtained, the plunger is moved rearward to close the probe inlet and the probe is retracted from the vessel and connecting device back into the sampler body bore.

An intended use of the sampler is in obtaining samples of wine in succession from a series of wine holding tanks. It is necessary to obtain for analysis samples of wine at various stages of the wine making process and, typically, the art contemplates that samples be withdrawn from a tank through an inline valve controlled hose connection near the bottom of the tank, such as at a bung opening to the tank. As wine ferments and ages the lees, comprising dead yeast cells and other solids, accumulates as a several inch thick layer of sediment on the inner tank wall in the region of the hose connection. To withdraw a valid wine sample free of sediment, the sample should be obtained from the tank at a location inward of the sediment layer, but that cannot readily be accomplished with conventional sampling techniques. The sampler of the invention, on the other hand, enables a valid, generally sediment-free sample of wine to be withdrawn from the tank, by virtue of the probe being extendable into the tank and through the sediment layer to a position where the inlet to the probe is in the wine 12 inches or more beyond the inner tank wall and beyond the inner boundary of the sediment layer, so that a relatively sediment free sample of wine flows into the probe inlet for collection. So that the same sampler might be used to successively draw wine samples from a series of tanks a separate connecting device, which as shown and described comprises a ball valve, is used at a bung opening to each tank to enable the sampler to be coupled to one tank to obtain a sample of wine from the tank, and to then be uncoupled from the tank for use in obtaining a sample of wine from another tank, without loss of wine from the tanks when the sampler is uncoupled.

To obtain a sample of wine, the sampler is attached to a closed connecting device at a bung opening to a wine holding tank, after which the connecting device is opened to establish communication between the sampler and tank interior. The sampler probe is then manually extended through the connecting device and bung opening into the interior of the tank a distance of 12 inches or more, until the inlet to the probe is in wine well beyond the inner boundary of the sediment layer. During extension of the probe, the plunger is maintained retracted under the positive pressure of wine in the tank to close the probe inlet and prevent sediment from entering the probe as the probe moves through the sediment layer. When the probe is fully extended into the tank it is locked against rearward retraction, at which point the probe inlet is positioned in the wine inward from the sediment layer. The sampler may then be flushed of any "carry over" from any previous sampling operation, which is accomplished by momentarily manually moving the plunger forward through the probe to briefly open the probe inlet for a flow of wine into and through the probe and to and out of a sample discharge port into a catch pan. The plunger is then allowed to retract under the pressure of wine in the tank to close the probe inlet, a sample collection container is positioned at the discharge port and the plunger is again manually moved forward to open the probe inlet for a flow of a wine sample, typically 500 cc of wine, through the probe and out of the discharge port into the sample collection container. After collection of the sample, the plunger is again allowed to be moved rearward under the pressure of wine to close the probe inlet, the sample container is removed for analysis of the wine sample and the probe is unlocked and slowly retracted from the tank and connecting device until its forward end is rearward of the connecting device. The connecting device is then closed to interrupt communication between the sampler and tank interior, whereupon the plunger is momentarily extended to relieve any trapped pressure of wine and to allow any wine retained in the sampler to drain into the catch pan. The sampler may then be detached from the connecting device for flushing with water and/or sanitizing solution before being coupled to a connecting device of another tank for obtaining the next wine sample.

Referring to the drawings, the sampler is indicated generally at 20 and is for obtaining generally sediment free samples of wine from a body of wine 22 contained in a large wine fermenting or holding tank 24. As the wine ferments and also while it settles and ages, the lees deposits as a several inch thick layer of sediment on the bottom and lower walls of the tank, including in the region of a bung opening 28 in a vertical side of the tank. A connecting device, indicated generally at 30, couples the sampler to the tank at the bung opening for access by the sampler to wine in the tank through the connecting device and bung opening. The connecting device may be a ball valve as shown, and includes a valve body 32 within which a ball 34 is rotated by a handle 36 between open and closed states. A passage 38 extends through the ball and a passage 40 extends through the valve body. A forward end of the valve body is mounted to the tank with its passage 40 in communication with the bung opening 28. In the open state of the ball 34 its passage 38 is generally aligned and in communication with the valve body passage 40 and the bung opening 28, and in a closed state the ball its passage is out of communication with the valve body passage and bung opening. A male coupling 42 having an inner passage 44 is at a rearward end of the valve body. The sampler 20 is attached to and detached from the ball valve via the male coupling, as will be described.

The sampler 20 includes an outer tubular body 46 having a longitudinal bore 48 and rearward and forward openings 50 and 52. Two radially inward extending annular shoulders are in the bore, comprising a first shoulder 54 at the front of the bore and a second shoulder 56 toward the rearward end of the bore. A bushing 58 is on the shoulder 56 and a bushing 60 is in the bore behind an annular shoulder 62 that extends radially inward slightly less than does the shoulder 54. An O-ring 64 is on the shoulder 62 between the bushing 60 and shoulder 54.

A tubular probe 66 extends through the sampler body bore 48. The probe is supported for forward and rearward reciprocation in the bore by the bushings 58 and 60 and is sealed with the bore by the Bring 64. A passage 68 extends through the probe between rearward and forward passage openings 70 and 72, and handles 74 and 76 are toward a rearward end of the probe for manual reciprocation of the probe through the sampler body bore. A passage 78 extends through the handle 76 between a sample outlet 80 from the probe passage 68 and a sample discharge port 82 from the handle passage, so that a sample of wine flowing through the probe passage flows into and through the sample outlet and handle passage to and out of the discharge port into a sample collection container 86, as will be described. An O-ring 84 around a lower end of the handle 76 provides a "soft" stop for the sample collection container when a neck of the container is extended around the handle to receive a sample from the discharge port 82. The O-ring serves to limit the extent to which the neck of the container may be extended around the handle to prevent breakage of the neck should the container be pivoted relative to the handle. To facilitate placement of the container neck around the handle, the handle is provided with a curved surface at its lower end to guide the neck around the handle.

The probe 66 carries both a cylindrical lock-pin 88 extending radially outward from a position slightly forward from the handles 74 and 76 and a retraction stop circlip 90 located slightly rearward from its forward end. An L-shaped lock slot in a rearward end of the sampler body 46 is adapted to receive the lock-pin and includes a longitudinal slot portion 92 that opens at the rearward end of the sampler body and extends forward to one end of a circumferential slot portion 94 of about 90° arcuate extent, an opposite end of which is provided with a detent 95. The arrangement is such that when the probe is extended forward through the sampler body, the lock-pin enters and moves to the forward end of the longitudinal slot 92 where it engages the sampler body and blocks further extension of the probe. The probe is then rotated to move the lock-pin into and through the circumferential slot 94 to and into the detent 95 to lock the probe against retraction from the sampler body under the positive pressure of wine 22 in the tank 24, with the positive pressure of wine serving to hold the lock-pin in the detent to prevent accidental rotation of the probe and lock-pin to the unlocked position. When the probe is to be retracted, it is manually pushed forward to move the lock-pin out of the detent and then rotated in the reverse direction to move the lock-pin out of the circumferential slot and into the longitudinal slot, at which point the probe is slowly moved rearward under manual control until further retraction is blocked by engagement of the circlip 90 with the front of the sampler body.

A generally cylindrical plunger 96 extends through the probe passage 68. Toward its rearward end the plunger is supported for reciprocation in the probe passage by a bushing 98 located between the rearward end of the probe passage and a radially inward extending annular shoulder 100. Toward its forward end a tip 102 of the plunger is supported for reciprocation by a reduced diameter forward end portion 104 of the probe passage. The tip has a generally hemispherical forward end 106 of a diameter greater than that of the probe passage inlet 72 and an O-ring seal 108 is in an annular recess in the tip just behind the forward tip end 106. When the plunger retracts, the O-ring moves against a chamfer 110 on the probe 66 at the probe passage inlet to close the inlet, such that the O-ring and chamfer act as a valve and valve seat. Toward a rearward end of the probe an O-ring 112 on the shoulder 100, between the front of the bushing 98 and a radially inward extending annular shoulder 114, seals between the probe and plunger. A plunger pushbutton 116 is attached by a fastener 118 to a rearward end of the plunger for manual reciprocation of the plunger in the probe.

Figure 1:
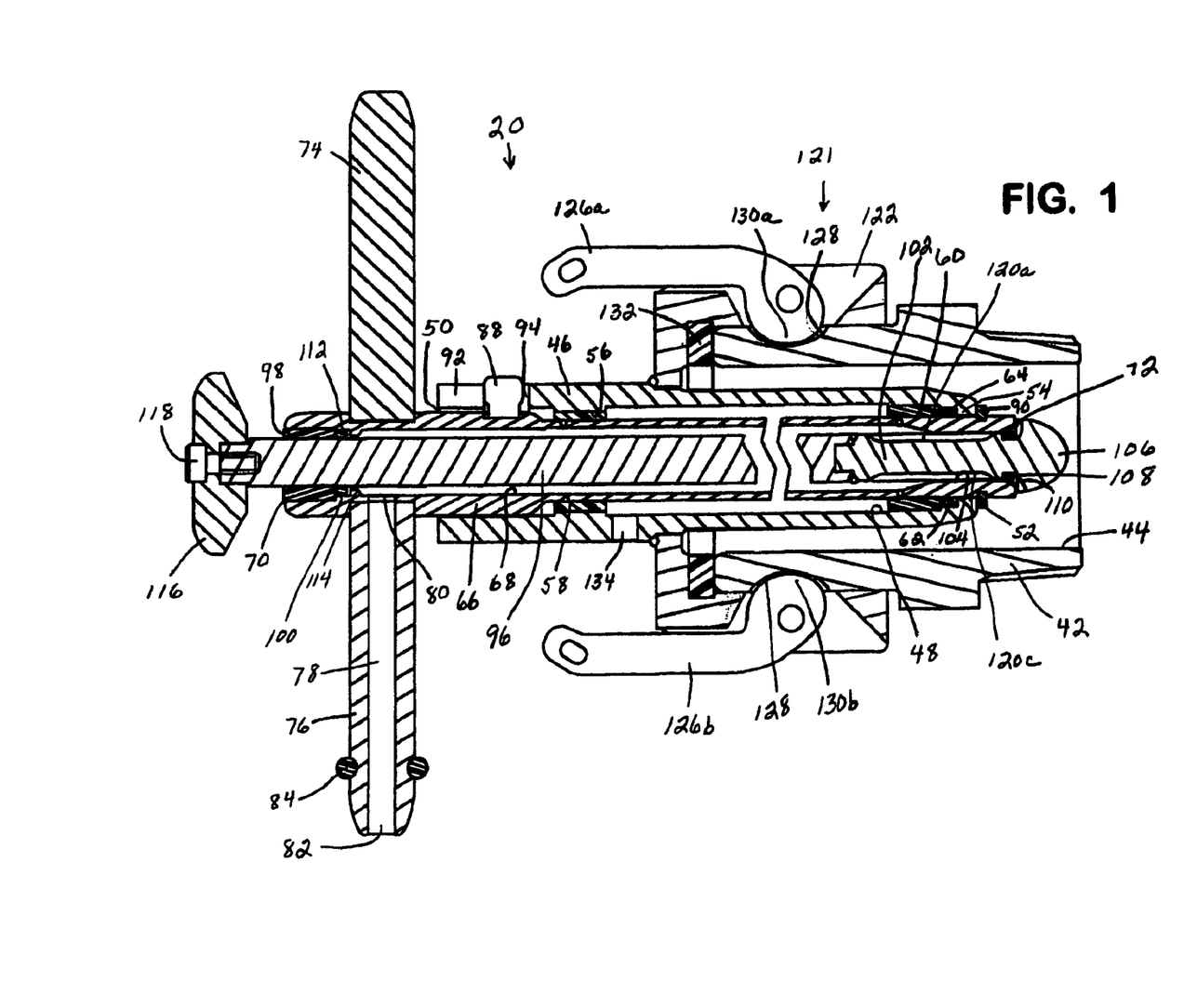
FIG. 1 is a cross-sectional side elevation view of a sampler embodying the teachings of the invention.
Figure 2A:
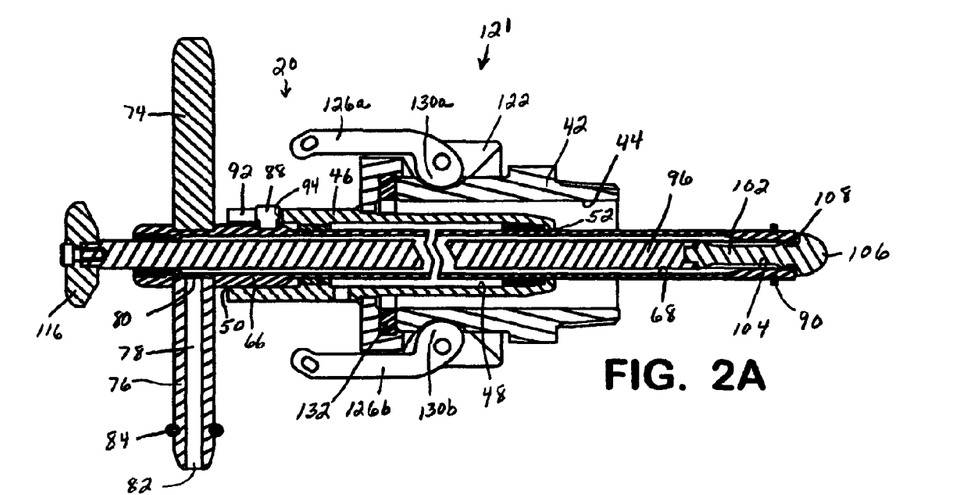
FIG. 2A is a cross-sectional side elevation view of the sampler, showing a probe of the sampler extended and a plunger in the probe retracted to close a forward liquid sample receiving inlet to the probe.
Figure 2B:
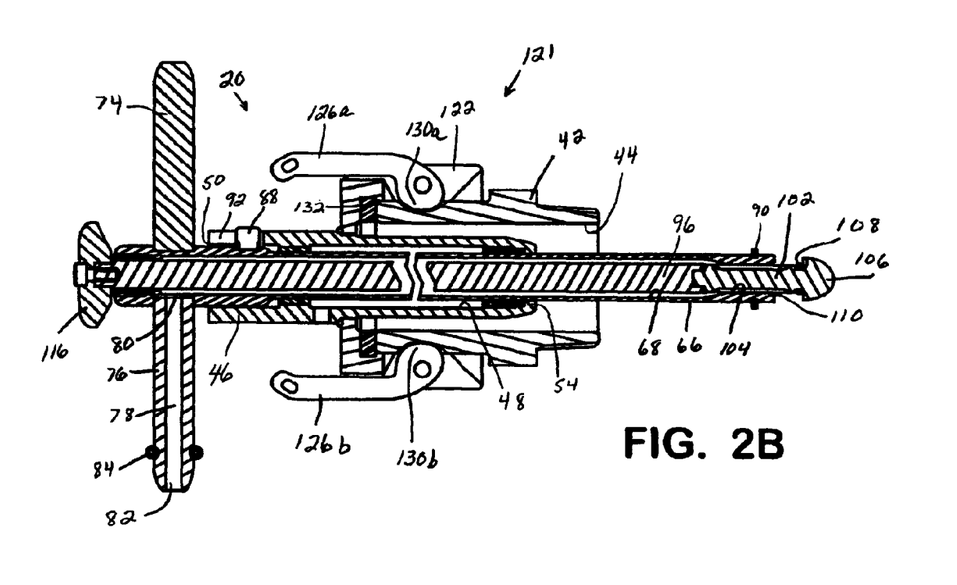
FIG. 2B is similar to FIG. 2A, except that the plunger is extended to open the probe inlet.
Figures 3, 4, 5:
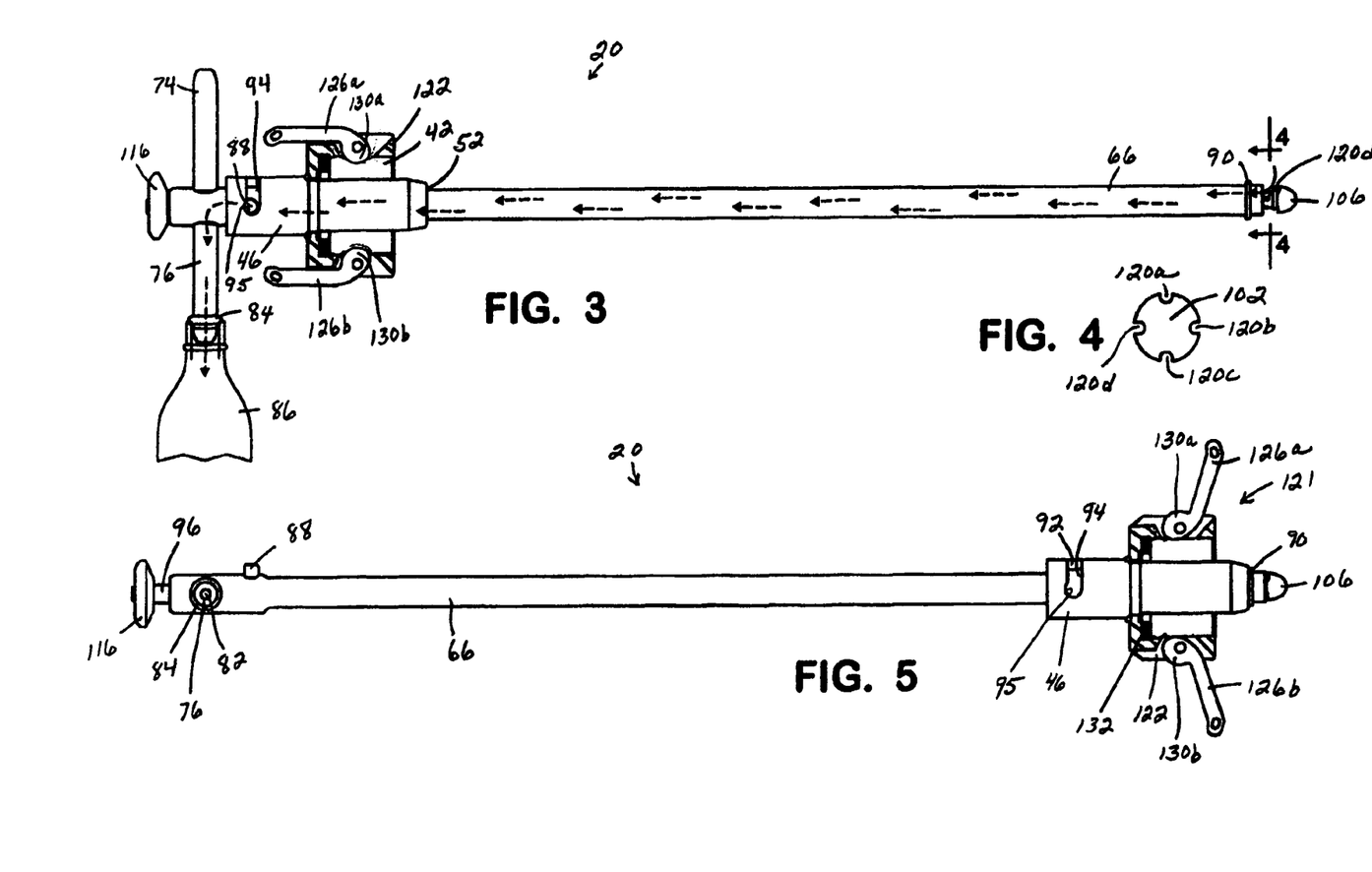
FIG. 3 is a side elevation view of the sampler with the probe extended, showing the flow path of a liquid sample through the sampler.
FIG. 4 is a cross-sectional view taken substantially along the lines 4—4 of FIG. 3, showing a forward tip of the plunger.
FIG. 5 is a side elevation view of the sampler with the probe retracted.
Figure 6:
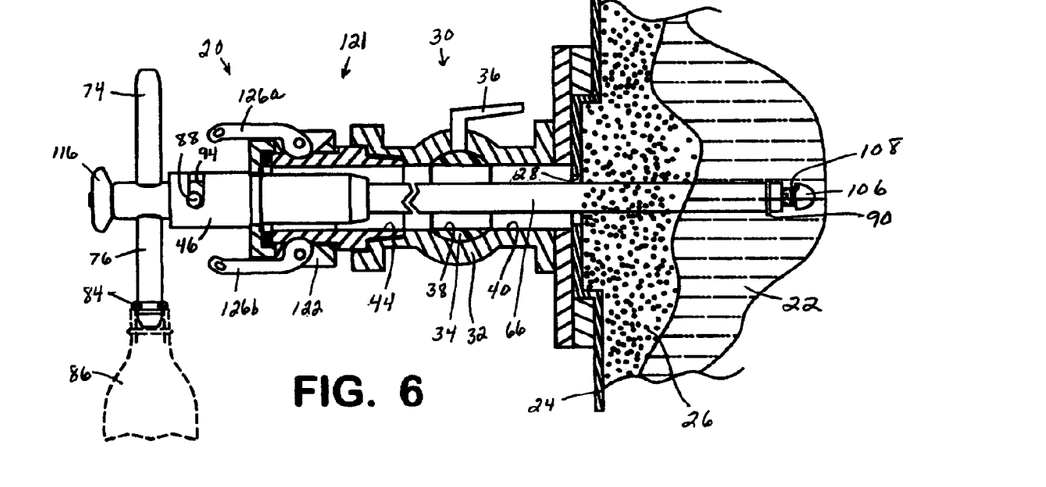
FIG. 6 is a side elevation view, partly in cross-section, showing the sampler coupled to a wine tank through an open connecting device and the probe extended through the connecting device to obtain a sample of wine from within the tank.
Figure 7:
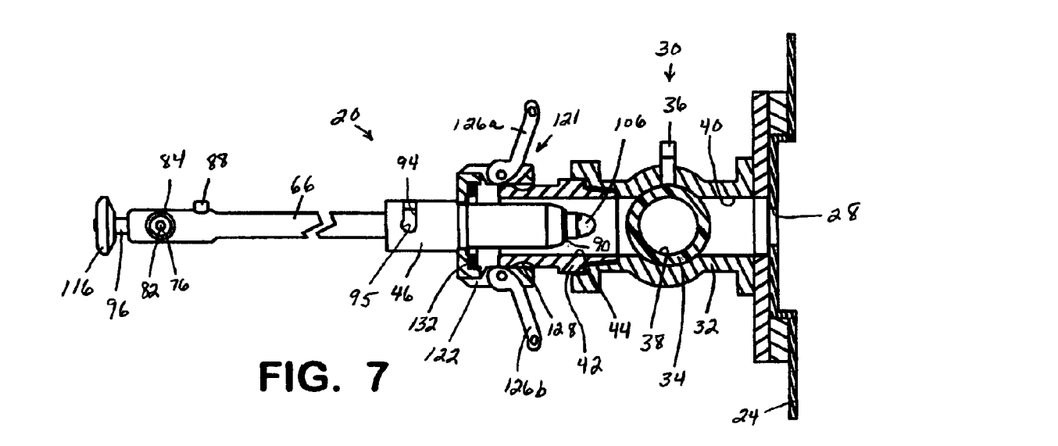
FIG. 7 is similar to FIG. 6, except that the probe is retracted and the connecting device is closed for disconnecting the sampler from the connecting device without outflow of wine from the tank.

The probe 66 is adapted to be manually extended forward through the sampler body bore 48 until it is fully extended to a sampling position, at which point the forward end of the probe, when the sampler 20 is coupled to the tank 24 by the connecting device 30, has been moved into the tank and the probe inlet 72 is in wine 22 to be sampled. With the probe in its sampling position, the plunger 96 is then manually pushed forward through the probe passage to move the plunger tip 102 partially out of the probe passage inlet, which moves the tip seal 108 off of the probe chamfer 110 and opens the probe inlet for flow of a sample of wine into and through the probe passage 68. Because the plunger tip is supported for reciprocation by the reduced diameter forward end portion 104 of the probe passage, the outer diameter of the plunger tip is just slightly smaller than the inner diameter of the probe passage forward end portion. Therefore, to accommodate a free flow of a wine sample past the plunger tip and into and through the probe passage, the outer surface of the plunger tip is longitudinally channeled. As best seen in FIGS. 1 and 4, four longitudinally extending channels 120a–d are formed in the plunger tip surface at about 90° arcuate spacings. The channels extend partially along the length of the tip, such that forward ends of the channels begin a short distance behind the O-ring 108, from which point the channels extend rearward a distance greater than the longitudinal length of the probe passage portion 104. The arrangement is such that when the plunger is extended to open the probe passage inlet, forward ends of the channels are moved out of the probe passage inlet, while rearward ends of the channels continue to extend rearward behind the reduced diameter probe passage portion 104. The channels then provide paths through which wine flows from the probe inlet to the probe passage rearward from the reduced diameter portion of the passage, where the flow path through the probe passage becomes annular and is defined between the inner surface of the probe passage and the outer surface of the plunger. Wine flowing through the probe passage flows into and through the sample outlet 80 and the handle passage 78 to and out of the discharge port 82 for collection in the container 86, with the "soft" stop 84 not preventing passage therepast of air displaced from the container by the wine sample.

The sampler 20 is adapted to be connected to and disconnected from individual ones of a plurality of male couplings 42 of ball valve connecting devices 30 provided on and in communication with bung openings 28 to each of a plurality of different wine tanks 24, so that the same sampler may be used to obtain samples of wine in succession from a series of wine tanks. To connect the sampler to the male couplings a female coupling, indicated generally at 121 and having a cup-shaped body 122 is attached to the sampler body 46. To accommodate releasable attachment of the male and female couplings, a cam and groove arrangement is used. The cam includes diametrically opposed rotatable cam arms 126a–b on the female coupling and the groove comprises an annular recess 128 in the male coupling. The forward end of the sampler extends beyond an open forward end of the female coupling, and in attaching the sampler to a male coupling, the front of the sampler is inserted into the passage 44 through the male coupling and the female coupling is extended around and receives the male coupling. The cam arms 126a–b are then rotated from radially outward extending positions to radially inward horizontal positions to move respective cam arm lobes 130a–b into the groove in the male coupling to draw the couplings together and attach the sampler 20 to the ball valve 30. A compressible annular gasket 132 is at an inner end of the female coupling, and when the couplings are drawn together and attached, the gasket is engaged and compressed by the rearward end of the male coupling. The gasket serves two purposes. When the sampler extracts a wine sample, wine fills the area within the male coupling and the gasket provides a seal preventing leakage of wine out of the couplings. In addition, when the cam arms are rotated to lock the couplings together, compression of the gasket not only enhances its sealing ability, but the gasket then maintains a tension between the couplings that stabilizes the connection and inhibits accidental rotation of the cam arms and inadvertent detachment of the couplings.

To obtain a sample of wine 22 from the tank 24, and beginning with the sampler 20 detached from the ball valve connecting device 30 and the ball valve closed, the sampler probe 66 is fully retracted through the sampler body 46, the front of the sampler is extended into the passage 44 through the ball valve male coupling 42 and the female coupling 121 is extended around the male coupling. The female coupling cam arms 126a–b are then rotated from their radially outward to their horizontal positions to move their cam lobes 130a–b into the annular groove 128 in the male coupling to draw the couplings together and attach the sampler to the ball valve. In this connection, the female coupling is attached the sampler body 46 in such rotational orientation with the sampler body that when the cam arms are radially outward and extending vertically, the probe handles 74 and 76, when the probe is in its sampling position, will also extend vertically. Consequently, joining the male and female couplings with the cam arms extending vertically and the longitudinal slot portion 92 facing upward will ensure that the handles are properly vertically oriented, with the handle 76 toward the bottom, for receiving and delivering a wine sample to the sample collection container 86. The ball valve is then opened by rotation of the ball 34, via its handle 36, so that the ball passage 38 extends and establishes communication between the probe and the bung opening 28 to the tank.

With the ball valve 30 open, the sampler handles 74 and 76 are manually pushed forward to extend the sampler probe 66 and plunger 96 forward, against the positive pressure of wine 22, through the sampler body 46 and out of the forward body bore opening 52 into and through the male coupling 42, ball valve passage 38 and bung opening 28 into the interior of the tank 24. While the plunger is moving forward, the pressure of the wine on the forward end 106 of the plunger tip 102 urges the plunger rearward, relative to the probe, to hold the plunger tip seal 108 against the probe chamfer 110 and close the probe inlet 72. By keeping the probe inlet closed during extension of the probe, when the probe moves into and through the sediment layer 26, entry of sediment into the probe, clogging of the probe passage 68 and subsequent contamination of the wine sample to be obtained are prevented. When the probe is fully extended to the point where its lock-pin 88 moves into and engages the forward end of the longitudinal slot 92 in the sampler body, the probe is in its sampling position and its forward inlet is located in generally sediment free wine 24, inward from the sediment 26, at which point the probe is rotated clockwise (as viewed from behind the probe) to move the lock-pin into and through the circumferential slot 94 and into the detent 95 to lock the probe against accidental counterclockwise rotation and rearward retraction under the urging of the positive pressure of wine. The probe is then flushed clean of any internal "carry over" residue remaining from a previous sampling operation by momentarily manually pressing the plunger push-button 116 to move the plunger tip 102 forward and unseat its seal 108 from the probe chamfer 110. This opens the probe inlet 72 for a flushing flow of wine from the tank into the inlet and into and through the probe tip channels 120a–d, the probe passage 68, the sample outlet 80, the handle passage 78 and the sample discharge port 82 into the catch pan. The pushbutton is then released to allow the plunger to retract under the urging of the pressure of the wine, although the push-button may also be manually pulled rearward, if necessary, to reseat the seal 108 against the chamfer 110 and close the probe inlet 72. The neck of the sample collection container 86 is then extended around the lower end of the sampler handle 76 until it abuts the O-ring stop 84.

With the sampler probe 66 fully extended to its sampling position, obtaining a sample of wine is accomplished in a manner similar to flushing the sampler. With the sample collection container 86 in place around the discharge port 82 at the bottom of the handle 76, the plunger push-button 116 is manually pushed forward to move the plunger 96 forward against the pressure of wine 22 in the tank 24, which unseats the plunger tip seal 108 from the probe chamfer 110 and opens the probe inlet 72 for a flow of wine from the tank into and through the probe inlet, the plunger tip channels 120a–d, the probe passage 68, the probe sample outlet 80, the handle passage 78 and the discharge port into the sample collection container. Any desired size sample may be taken, although a typical sample size is on the order of about 500 cc. During flow of the wine sample from the tank, the O-ring 64 prevents entry of wine between the sampler body and probe and into the sampler body bore 48, although a vent opening 134 in the sampler body provides an outlet for any wine that may enter the bore. Also during flow of the wine sample, the O-ring 112 seals between the plunger and probe to prevent leakage of wine out of the rearward probe opening 70. After a desired volume wine sample is flowed into the container, the plunger push-button 116 is released for rearward movement of the plunger under the pressure of wine in the tank to close the probe inlet 72 and the sample collection container is removed for analysis of the wine sample. The probe is then manually pushed slightly forward, via the handles 74 and 76, to move the lock-pin 88 out of the detent 95, after which the probe is rotated counterclockwise to move the lock-pin out of the circumferential slot 94 and into the longitudinal slot 92, at which point the probe may be slowly withdrawn, under manual control, from the tank and through the ball valve until the retraction stop circlip 90 engages the front of the sampler body 46. When the probe and plunger are fully retracted and out of the ball valve passage 38, the ball valve is closed to interrupt communication between the sampler and bung opening to the tank. The plunger push-button is then briefly pressed to open the probe inlet and relieve any trapped pressure of wine within the ball valve, with any wine then draining out of the sampler being caught in the catch pan. The cam locking levers 126a–b of the female coupling 122 are then rotated to their vertical positions to move their cam lobes 130a–b out of the male coupling groove 128 and detach the sampler 20 from the ball valve 30, with any remaining residual wine in the couplings falling into the catch pan.

The sampler 20 is adapted to be coupled with ball valves 30 individually associated with each of a number of different wine holding tanks 24, in order to obtain wine samples in succession from a series of tanks. The sampler may therefore be cleaned between sampling operations to prevent cross-contamination of samples, and while it is uncoupled from a ball valve it can be flushed with water and/or sanitizing solution. For a more thorough cleaning and sanitizing, the plunger push-button 116 can be removed from the plunger 96 to permit the plunger to be withdrawn out of the front of the probe 66. Then, with the retraction stop circlip 90 removed from the front of the probe, the probe can be withdrawn out of the rear of the sampler body 46. Such disassembly provides access to the bring seals 64,108 and 112, which can be removed for sanitizing or replacement.

While one embodiment of the invention has been described in detail, various modifications and other embodiments thereof can be devised by one skilled in the art without departing from the spirit and scope of the invention, as defined in the accompanying claims.

What is claimed is:

1. A sampling apparatus for obtaining samples of liquid product from a vessel, comprising:

a sampler including a body having a longitudinal bore with forward and rearward openings to said bore, an elongate probe in said bore and having a longitudinal passage with a forward inlet to and a rearward sample outlet from said passage, means for opening and closing said probe passage inlet, and means for reciprocating said probe in said bore to extend said probe out of and to retract said probe into said bore forward opening; and a connecting device for being mounted to the vessel, wherein said sampler is attachable to and detachable from said connecting device and said connecting device is operable between open and closed states to respectively place said sampler into and to take said sampler out of communication with liquid product in the vessel, said sampler being detachable from said connecting device, without escape of liquid product from the vessel, when said connecting device is in said closed state, said reciprocating means, when said connecting device is in said open state, being operable to extend said probe forward through said sampler body bore forward opening and said connecting device into the vessel to a sampling position of said probe, relative to said body, where said probe passage inlet is in liquid product in the vessel, and to then retract said probe from the vessel and through said connecting device and sampler body bore forward opening, and said opening and closing means being operable to close said probe passage inlet while said reciprocating means extends said probe forward to said probe sampling position, to open said probe passage inlet while said probe is in said sampling position for flow of a sample of liquid product from the vessel into said probe inlet and through said probe passage to said sample outlet, and to then close said probe inlet while said probe is retracted.

2. A sampling apparatus as in claim 1, wherein said opening and closing means and said reciprocating means are manually operated.

3. A sampling apparatus as in claim 1, wherein said connecting device is for being attached to the vessel in communication with an opening to the vessel and said reciprocating means extends said probe through and retracts said probe from the vessel opening.

4. A sampling apparatus as in claim 1, including bearing means and seal means in said sampler body bore for supporting said probe for reciprocation in said bore and for sealing said probe to said sampler body.

5. A sampling apparatus as in claim 1, wherein said connecting device includes a valve operable between said open and closed states and having a passage that extends between said sampler and the vessel when said valve is in said open state for movement of said sampler probe through said valve passage to said sampling position and that does not extend between said sampler and the vessel when said valve is in said closed state and said probe is retracted from said valve passage.

6. A sampling apparatus as in claim 5, wherein said connecting device valve includes a shell and a ball valve within said shell, and said ball valve has said valve passage extending therethrough and is manually rotatable to said open state where said passage extends between said sampler and the vessel interior and said closed state where said passage does not extend between said sampler and the vessel interior.

7. A sampling apparatus as in claim 1, wherein a rearward end of said probe extends rearward out of said sampler body bore rearward opening and said means for reciprocating said probe in said bore comprises manually movable handle means attached to said probe rearward of said bore rearward opening.

8. A sampling apparatus as in claim 7, including a passage in said handle means extending between said probe sample outlet and a sample discharge port from said handle passage for flow of a sample of liquid product from the vessel into said probe inlet and through said probe passage to and through said probe sample outlet and handle passage to and out of said sample discharge port for collection.

9. A sampling apparatus as in claim 1, including locking means operable when said probe is extended to its sampling position for releasably locking said probe against retraction through said sampler body bore.

10. A sampling apparatus as in claim 9, wherein said locking means includes slot means in said sampler body and a lock-pin extending from said probe for entry into said slot means when said probe is extended through said body to said sampling position.

11. A sampling apparatus as in claim 1, wherein said probe passage inlet opening and closing means includes an elongate plunger extending through said probe passage, means for manually reciprocating said plunger between forward and rearward positions in said probe passage, and valve means for opening and closing said probe passage inlet in response to said plunger being in respective forward and rearward positions.

12. A sampling apparatus as in claim 11, wherein said probe passage has a rearward opening and said plunger extends rearward out of said rearward opening, and said reciprocating means comprises means toward a rearward end of said plunger for manually reciprocating said plunger is said probe passage.

13. A sampling apparatus as in claim 11, wherein said valve means for opening and closing said probe passage inlet comprises a valve seat on one of said probe and plunger and a valve on the other, said valve and valve seat moving together to close said probe passage inlet when said plunger is reciprocated to its rearward position and said valve and valve seat moving apart to open said probe passage inlet when said plunger is reciprocated to its forward position.

14. A sampling apparatus as in claim 11, wherein the sample of liquid product from the vessel flows around said plunger when flowing through said probe passage.

15. A sampling apparatus as in claim 11, including means for supporting said plunger for reciprocation in said probe passage and means for sealing said plunger to said probe to prevent leakage of sampled liquid product out of said probe passage.

16. A sampling apparatus as in claim 11, wherein said plunger includes a tip extending forward through said probe passage inlet and said tip has a forward end positioned forward from said probe inlet and of a greater diameter than said inlet, and said valve means for opening and closing said probe passage inlet comprises a valve seat formed on said probe at said probe passage inlet and seal means carried by said plunger tip rearward from said tip forward end and forward from said probe valve seat, said seal means moving against said valve seat to close said probe passage inlet when said plunger is reciprocated to its rearward position and said seal means moving away from said valve seat to open said probe passage inlet when said plunger is reciprocated to its forward position.

17. A sampling apparatus as in claim 16, wherein said plunger is cylindrical and rearward from its forward tip is of a smaller diameter than said probe passage for flow of a liquid product sample through said probe passage and around said plunger.

18. A sampling apparatus as in claim 17, wherein said plunger tip is generally cylindrical and extends through a reduced diameter forward end portion of said probe passage, said plunger tip has an outside diameter that is slightly smaller than the inside diameter of said reduced diameter probe passage portion and said reduced diameter probe passage portion supporting said plunger tip for reciprocation therein and including at least one longitudinally extending channel in an outer surface of said plunger tip for accommodating a flow of a liquid product sample past said tip and said reduced diameter probe passage portion into said probe passage rearward from said tip.

19. A sampling apparatus as in claim 18, wherein said at least one longitudinally extending channel comprises a plurality of arcuately spaced longitudinally extending channels in said plunger tip outer surface.

20. A sampling apparatus as in claim 1, further including a male and a female coupling, wherein one of said couplings is attached to said sampler body and said connecting device includes the other of said couplings, said couplings being joined together to attach said sampler to said connecting device.

21. A sampling apparatus as in claim 20, including means for releasably locking said couplings together so that said sampler may be securely attached to and detached from said connecting device.

22. A sampling apparatus for obtaining samples of wine from a wine holding tank having an opening toward a lower end of the tank and in which lees forms a sediment layer in the region of the opening, comprising:
  a sampler including a body having a longitudinal bore with forward and rearward openings to said bore, an elongate tubular probe extending through said bore and having a longitudinal passage with a forward inlet to, a rearward opening to, and a sample outlet from said passage, said probe having a length greater than that of said body bore, means for manually opening and closing said probe inlet, and means for manually reciprocating said probe in said bore to extend said probe forward out of and to retract said probe rearward into said bore forward opening;
  a connecting device for being mounted to the tank in communication with the tank opening, wherein said sampler is attachable to and detachable from said connecting device and said connecting device is operable between open and closed states to respectively establish a path for reciprocation of said probe forward through said connecting device and the tank opening to a sampling position of said probe relative to said body, where said probe inlet is positioned in wine in the tank and to interrupt said path when said probe is reciprocated rearward out of said connecting device, said sampler being detachable from said connecting device, without escape of wine through the tank opening, when said connecting device is in said closed state,
  said means for manually reciprocating, when said connecting device is in said open state, being operable to extend said probe forward through said connecting device, the tank opening and any sediment in the region of the tank opening to said probe sampling position where said probe passage inlet is in wine in the tank beyond any sediment layer, and to then retract said probe from the tank and through the tank opening and said connecting device, and
  said means for manually opening and closing being operable to close said probe passage inlet while said reciprocating means extends said probe to said probe sampling position, to open said probe passage inlet while said probe is in said sampling position for flow of a sample of wine from the tank into said probe inlet and through said probe passage to said probe passage sample outlet, and to then close said probe inlet while said probe is retracted, whereby said probe inlet is closed whenever said inlet moves through any sediment layer so that any sediment in the tank is prevented from entering said probe inlet.

23. A sampling apparatus as in claim 22, including bearing means and seal means for supporting said sampler probe for reciprocation in said sampler body bore and for sealing said probe to said bore.

24. A sampling apparatus as in claim 22, further including a male and a female coupling, wherein one of said couplings is attached to said sampler body and said connecting device includes the other of said couplings, and means for releasably locking said couplings together so that said sampler may be attached to and detached from said connecting device.

25. A sampling apparatus as in claim 22, wherein said connecting device includes a valve operable between said open and closed states, said valve has a passage that extends between said sampler and the vessel opening when said valve is in said open state for extension of said sampler probe through said valve passage and the tank opening to said probe sampling position, and that does not extend between said sampler and the vessel opening when said valve is in said closed state and said probe is retracted.

26. A sampling apparatus as in claim 25, wherein said connecting device valve includes a shell and a ball valve in said shell, and said ball valve has said valve passage extending therethrough and is manually rotatable to said open state where said passage extends between said sampler and the vessel opening and to said closed state where said passage does not extend between said sampler and the vessel opening.

27. A sampling apparatus as in claim 22, wherein a rearward end of said probe extends rearward out of said bore rearward opening and said means for reciprocating said probe comprises handle means attached to said probe rearward from said bore rearward opening for being manually gripped and moved to reciprocate said probe in said bore.

28. A sampling apparatus as in claim 27, including a passage in said handle means extending between said probe passage sample outlet and a sample discharge port from said handle means passage for flow of a sample of wine from the vessel into said probe inlet and through said probe passage to and through said probe sample outlet and said handle means passage to and out of said sample discharge port for collection.

29. A sampling apparatus as in claim 22, including locking means operable when said probe is in said probe sampling position for releasably locking said probe against retraction.

30. A sampling apparatus as in claim 29, wherein said locking means includes L-shaped slot means having detent means in said sampler body and lock-pin means extending from said probe for entry into said slot means and detent means when said probe is extended to said sampling position.

31. A sampling apparatus as in claim 22, wherein said means for opening and closing said probe passage inlet includes a generally cylindrical plunger extending longitudinally through said probe passage, means for reciprocating said plunger between forward and rearward positions in said probe passage, and valve means for opening and closing said probe passage inlet in response to said plunger being in respective forward and rearward positions in said probe passage.

32. A sampling apparatus as in claim 31, wherein the sample of wine from the vessel interior flows into said probe inlet and around said plunger when flowing through said probe passage.

33. A sampling apparatus as in claim 31, including means for supporting said plunger for reciprocation in said probe passage and means for sealing said plunger to said probe.

34. A sampling apparatus as in claim 31, wherein a rearward end of said plunger extends rearward out of said probe passage rearward opening, a forward end of said plunger extends through said probe passage inlet, said reciprocating means comprises means toward a rearward end of said plunger for manually reciprocating said plunger in said probe passage, and said valve means for opening and closing said probe passage inlet comprises a valve seat on one of said probe and plunger and a valve on the other, said valve and valve seat moving together to close said probe passage inlet when said plunger is reciprocated to its rearward position and moving apart to open said probe passage inlet when said plunger is reciprocated to its forward position.

35. A sampling apparatus as in claim 34, wherein said plunger has a forward tip extending through and out of said probe passage inlet and said tip has an enlarged forward end positioned forward from and of a greater diameter than said probe passage inlet, said valve means seat is on said probe at said probe passage inlet and said valve is on said tip, said valve moving against said seat to close said probe passage inlet when said plunger is reciprocated to its rearward position and moving away from said seat to open said probe passage inlet when said plunger is reciprocated to its forward position.

36. A sampling apparatus as in claim 35, wherein said plunger is cylindrical and rearward from its forward tip is of a smaller diameter than said probe passage for flow of sampled wine through said probe passage and around said plunger, said plunger tip is generally cylindrical and extends through a reduced diameter forward probe passage portion having an inner diameter that is slightly greater than the outer diameter of said tip for supporting said plunger tip for reciprocation therein, and including at least one longitudinally extending channel in an outer surface of said tip for accommodating a flow of wine past said tip and through said reduced diameter probe passage portion.

37. A method of sampling a liquid product in a vessel, comprising the steps of:
coupling a sampler to an opening to the vessel with a connecting device;
establishing a path through the connecting device between the sampler and the opening to the vessel;
extending a probe of the sampler, in which probe there is an inlet, through the connecting device path and vessel opening and into the vessel to position the probe inlet in liquid product in the vessel;
closing the probe inlet during performance of said extending step;
opening the probe inlet, following performance of said extending step and while the inlet is in liquid product in the vessel, for flow of a sample of liquid product into the inlet;
retracting the probe from the vessel interior and through the vessel opening and connecting device; and
closing the probe inlet during performance of said retracting step.

38. A method as in claim 37, including the further step, following performance of said retracting step, of interrupting the path through the connecting device between the sampler and the vessel opening.

39. A method as in claim 38, including the further step, following performance of said interrupting step, of detaching the sampler from the connecting device without escape of liquid product from the vessel opening.

40. A method of obtaining samples of wine from a tank in which there is a sediment layer of the lees toward a lower end of the tank, comprising the steps of:
mounting a connecting device to the tank;
attaching a sampler to the connecting device;
establishing a path through the connecting device between the sampler and an opening to the tank;
extending a probe of the sampler having an inlet thereto, while maintaining the probe inlet closed, through the connecting device path, tank opening and sediment layer in the tank to position the probe inlet in wine in the tank inward from the sediment layer;
opening the probe inlet while the inlet is in wine in the tank inward from the sediment layer for flow of a sample of wine into the inlet;
closing the probe inlet after the sample of wine has flowed through the inlet; and
retracting the probe from the tank interior and through the sediment layer, tank opening and connecting device path while maintaining the probe inlet closed.

41. A method as in claim 40, including the step of flowing the wine sample, while the probe inlet is open, into the probe inlet and through the probe to a sample collection point beyond the connecting device.

42. A method as in claim 40, wherein said establishing, extending, retracting, opening and closing steps are manually performed.

43. A method as in claim 40, including the steps, following performance of said retracting step, of interrupting the path through the connecting device, and then detaching the sampler from the connecting device without escape of wine from the tank opening.

44. A method as in claim 40, including repeating said steps of obtaining samples of wine to obtain successive samples of wine from a series of different tanks of wine.

* * * * *